(12) United States Patent
Hasebe

(10) Patent No.: US 10,334,155 B2
(45) Date of Patent: Jun. 25, 2019

(54) IMAGING DEVICE AND CAPSULE ENDOSCOPE

(71) Applicant: OLYMPUS CORPORATION, Hachioji-shi, Tokyo (JP)

(72) Inventor: Hiroki Hasebe, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 100 days.

(21) Appl. No.: 15/359,885

(22) Filed: Nov. 23, 2016

(65) Prior Publication Data

US 2017/0078563 A1    Mar. 16, 2017

Related U.S. Application Data

(63) Continuation of application No. PCT/JP2015/063581, filed on May 12, 2015.

(30) Foreign Application Priority Data

Jun. 23, 2014   (JP) ................................. 2014-128040

(51) Int. Cl.
   *A61B 1/00* (2006.01)
   *H04N 5/232* (2006.01)
   (Continued)

(52) U.S. Cl.
   CPC ..... *H04N 5/23216* (2013.01); *A61B 1/00006* (2013.01); *A61B 1/00009* (2013.01);
   (Continued)

(58) Field of Classification Search
   CPC ..................................................... A61B 1/00
   See application file for complete search history.

(56) References Cited

U.S. PATENT DOCUMENTS

| | | | |
|---|---|---|---|
| 6,985,172 B1* | 1/2006 | Rigney | G06K 9/00335 348/149 |
| 7,940,973 B2* | 5/2011 | Lee | A61B 1/0002 348/699 |
| 2011/0095169 A1* | 4/2011 | Takenaka | H04N 5/3658 250/208.1 |

FOREIGN PATENT DOCUMENTS

| | | |
|---|---|---|
| EP | 2 662 016 A1 | 11/2013 |
| JP | 8-138058 A | 5/1996 |

(Continued)

OTHER PUBLICATIONS

International Search Report dated Jul. 14, 2015, issued in counterpart International Application No. PCT/JP2015/063581 (2 pages).

*Primary Examiner* — Rowina J Cattungal
(74) *Attorney, Agent, or Firm* — Westerman, Hattori, Daniels & Adrian, LLP

(57) ABSTRACT

An imaging device includes an imaging unit, a first change amount calculating unit, and a second change amount calculating unit, and a control unit. The imaging unit continuously performs imaging to generate images of a plurality of frames of which the resolution is any one of a plurality of resolutions. The first change amount calculation unit calculates a first change amount that is an information change amount of the images of a plurality of frames. The second change amount calculation unit calculates a second change amount that is a temporal change amount of the first change amount. The control unit controls a resolution of the imaging unit on the basis of a result of comparing the second change amount with a threshold value and a result of discriminating a sign of the second change amount.

2 Claims, 9 Drawing Sheets

(51) Int. Cl.
    *H04N 5/341*         (2011.01)
    *H04N 5/343*         (2011.01)
    *A61B 1/04*          (2006.01)
    *A61B 1/045*         (2006.01)
    *G02B 23/24*         (2006.01)
    *H04N 5/225*         (2006.01)

(52) U.S. Cl.
    CPC .......... *A61B 1/00016* (2013.01); *A61B 1/041* (2013.01); *A61B 1/045* (2013.01); *G02B 23/2484* (2013.01); *H04N 5/232* (2013.01); *H04N 5/23241* (2013.01); *H04N 5/23245* (2013.01); *H04N 5/341* (2013.01); *H04N 5/343* (2013.01); *H04N 2005/2255* (2013.01)

(56) References Cited

FOREIGN PATENT DOCUMENTS

| | | |
|---|---|---|
| JP | 2003-134386 A | 5/2003 |
| JP | 2013-128847 A | 7/2013 |
| JP | 2013-175824 A | 9/2013 |

\* cited by examiner

FIG. 7

| INFORMATION AMOUNT | ABSOLUTE VALUE OF SECOND CHANGE AMOUNT | PREVIOUS INFORMATION AMOUNT | EXAMPLE OF OPERATION |
|---|---|---|---|
| SMALLER THAN FIRST THRESHOLD VALUE | SMALLER THAN SECOND THRESHOLD VALUE | SMALLER THAN FIRST THRESHOLD VALUE | (1) SINCE SUBJECT IS NOT IMPORTANT SUBJECT AND THERE IS NO CHANGE IN SCENE, IMAGE IS NOT RECORDED. |
| | | GREATER THAN OR EQUAL TO FIRST THRESHOLD VALUE | (2) SINCE POSSIBILITY OF IMPORTANT SUBJECT HAS BECOME LOW, RESOLUTION IS SET TO LOW RESOLUTION AND IMAGE IS RECORDED. |
| | GREATER THAN OR EQUAL TO SECOND THRESHOLD VALUE | SMALLER THAN FIRST THRESHOLD VALUE | (3) SINCE POSSIBILITY OF IMPORTANT SUBJECT HAS BECOME VERY LOW, RECORDING OF IMAGE STOPS (SIGN IS NEGATIVE). OTHERWISE, SINCE POSSIBILITY OF IMPORTANT SUBJECT HAS BECOME VERY HIGH, RESOLUTION IS SET TO LOW RESOLUTION AND IMAGE IS RECORDED (SIGN IS POSITIVE). |
| | | GREATER THAN OR EQUAL TO FIRST THRESHOLD VALUE | (4) SINCE POSSIBILITY OF IMPORTANT SUBJECT IS LOW, BUT THERE IS CHANGE IN SCENE, RESOLUTION IS SET TO LOW RESOLUTION AND IMAGE IS RECORDED. |
| GREATER THAN OR EQUAL TO FIRST THRESHOLD VALUE | SMALLER THAN SECOND THRESHOLD VALUE | SMALLER THAN FIRST THRESHOLD VALUE | (5) RESOLUTION IS MAINTAINED AND IMAGE IS RECORDED. |
| | | GREATER THAN OR EQUAL TO FIRST THRESHOLD VALUE | (6) SINCE THERE IS POSSIBILITY OF IMPORTANT SUBJECT, BUT THERE IS POSSIBILITY OF NOISE, RESOLUTION IS SET TO MEDIUM RESOLUTION AND IMAGE IS RECORDED. |
| | GREATER THAN OR EQUAL TO SECOND THRESHOLD VALUE | SMALLER THAN FIRST THRESHOLD VALUE | (7) SINCE POSSIBILITY OF IMPORTANT SUBJECT HAS BECOME VERY HIGH, RESOLUTION IS SET TO HIGH RESOLUTION AND IMAGE IS RECORDED. |
| | | GREATER THAN OR EQUAL TO FIRST THRESHOLD VALUE | (8) SINCE POSSIBILITY OF IMPORTANT SUBJECT HAS BECOME VERY HIGH, RESOLUTION IS INCREASED AND IMAGE IS RECORDED (SIGN IS POSITIVE). OTHERWISE, SINCE POSSIBILITY OF IMPORTANT SUBJECT HAS BECOME VERY LOW, RESOLUTION IS DECREASED AND IMAGE IS RECORDED (SIGN IS NEGATIVE). |

IMAGING DEVICE AND CAPSULE ENDOSCOPE

Priority is claimed on Japanese Patent Application No. 2014-128040, filed Jun. 23, 2014, and this application is a continuing application based on International Patent Application No. PCT/JP2015/063581, filed May 12, 2015, the contents of the Japanese Application and the PCT Application are incorporated herein by reference.

BACKGROUND OF THE INVENTION

Field of the Invention

The present invention relates to an imaging device in which a resolution of an image can be changed, and a capsule endoscope.

Description of Related Art

A technology capable of limiting a data amount of an image to be recorded by autonomously changing a resolution of the image at the time of imaging is disclosed. For example, in a technology disclosed in Japanese Unexamined Patent Application, First Publication No. 2003-134386, when an information change amount of an image is large, the resolution is set to be high. Further, when the information change amount of the image is small, the resolution is set to be low.

SUMMARY OF THE INVENTION

According to a first aspect of the present invention, an imaging device includes an imaging unit that continuously performs imaging to generate images of a plurality of frames of which the resolution is any one of a plurality of resolutions; a first change amount calculation unit that calculates a first change amount that is an information change amount of the images of a plurality of frames; a second change amount calculation unit that calculates a second change amount that is a temporal change amount of the first change amount; and a control unit that controls a resolution of the imaging unit on the basis of a result of comparing the second change amount with a threshold value and a result of discriminating a sign of the second change amount.

According to a second aspect of the present invention, in the imaging device according to the first aspect, the imaging unit includes a plurality of pixels that generate first pixel signals based on incident light; a plurality of first accumulation units that accumulate the first pixel signals output from the plurality of pixels; a first output unit that outputs the images of the plurality of frames composed of the first pixel signals accumulated in the plurality of first accumulation units; a plurality of second accumulation units that accumulate second pixel signals obtained by adding the first pixel signals output from the plurality of pixels for every plurality of pixel signals; and a second output unit that outputs the images of the plurality of frames composed of the second pixel signals accumulated in the plurality of second accumulation units.

According to a third aspect of the present invention, in the imaging device according to the first aspect, the control unit controls the resolution of the imaging unit on the basis of a result of comparing the information amount of the image with a first threshold value, a result of comparing the second change amount with a second threshold value, and a result of discriminating the sign of the second change amount.

According to a fourth aspect of the present invention, a capsule endoscope includes the imaging device according to the first aspect.

BRIEF DESCRIPTION OF THE DRAWINGS

FIG. 7 is a reference diagram showing content of control performed by a control unit included in the imaging device according to a modification example of the first embodiment of the present invention.

DETAILED DESCRIPTION OF THE INVENTION

Hereinafter, embodiments of the present invention will be described with reference to the accompanying drawings.

(First Embodiment)

Figure 1:
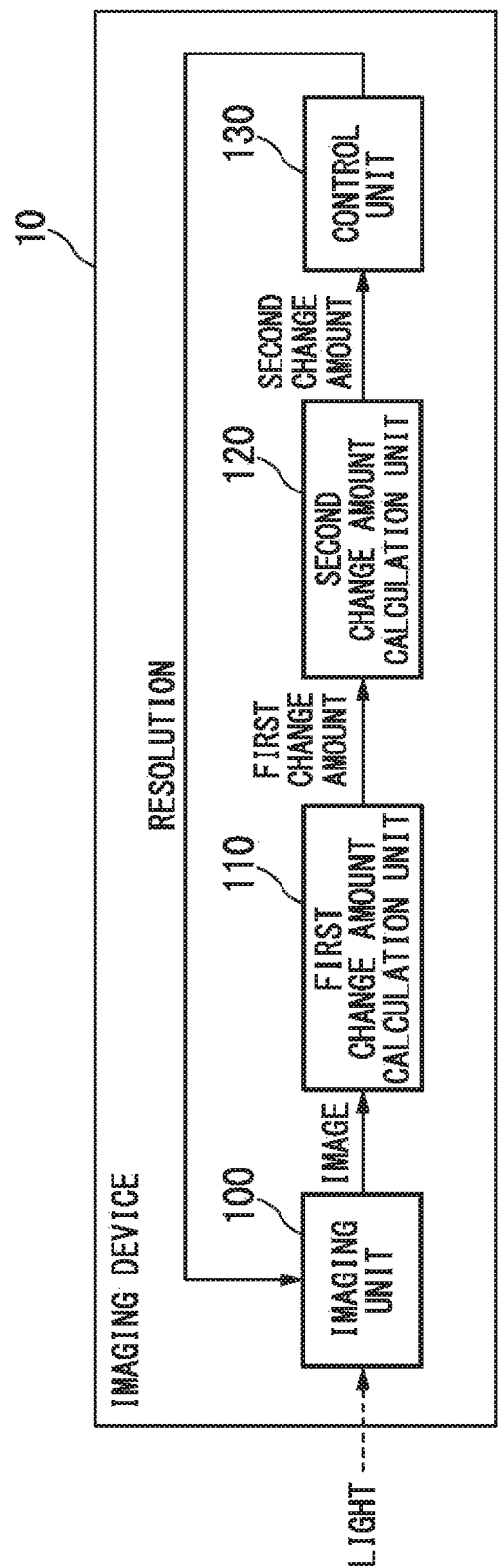
FIG. 1 is a block diagram showing a configuration of an imaging device according to a first embodiment of the present invention.

First, a first embodiment of the present invention will be described. FIG. 1 shows a configuration of an imaging device 10 according to this embodiment. As shown in FIG. 1, the imaging device 10 includes an imaging unit 100, a first change amount calculation unit 110, a second change amount calculation unit 120, and a control unit 130.

The imaging unit 100 continuously performs imaging to generate an image (image signal) of a plurality of frames. The resolution of the image is one of a plurality of resolutions. One of the plurality of resolutions can be set in the imaging unit 100. Further, the resolution that is set in the imaging unit 100 can be changed.

The first change amount calculation unit 110 calculates first change amounts which are information change amounts of images of a plurality of frames. For example, the first change amount is a sum of absolute values of differences between image signals in images of two frames captured at different times. Alternatively, the first change amount may be a sum of absolute values of differences between information amounts (feature amounts) generated from image signals in images of two frames captured at different times. For example, the first change amount calculation unit 110 calculates first change amounts of images of two consecutive frames. The first change amount calculation unit 110 may calculate first change amounts of images of n (n is a natural number) frames and images of n+k frames for every k (k is a natural number greater than or equal to 2) frames. The first change amount calculation unit 110 may include a storage unit that stores images of a plurality of frames. Alternatively, a storage unit that stores images output from the imaging unit 100 may be provided separately from the first change amount calculation unit 110.

The second change amount calculation unit 120 calculates a second change amount that is a temporal change amount of the first change amounts. For example, the second change amount calculation unit 120 calculates a second change amount on the basis of two first change amounts that are continuously calculated. To facilitate a process performed by the control unit 130, the second change amount may be an absolute value of the temporal change amount. When the second change amount is an absolute value, the imaging device 10 holds a sign (positive and negative) of the second change amount together with the second change amount.

The control unit 130 controls a resolution of the imaging unit 100 on the basis of a result of comparing the second change amount with a threshold value. For example, when the second change amount is smaller than the threshold value, the control unit 130 sets the resolution of the imaging unit 100 to a first resolution. Further, when the second change amount is greater than or equal to the threshold value, the control unit 130 sets the resolution of the imaging unit 100 to a second resolution higher than the first resolution. It is desirable for the control unit 130 to control the resolution of the imaging unit 100 on the basis of a result of comparing the second change amount with the threshold value and a result of discriminating the sign of the second change amount.

Figure 2A:
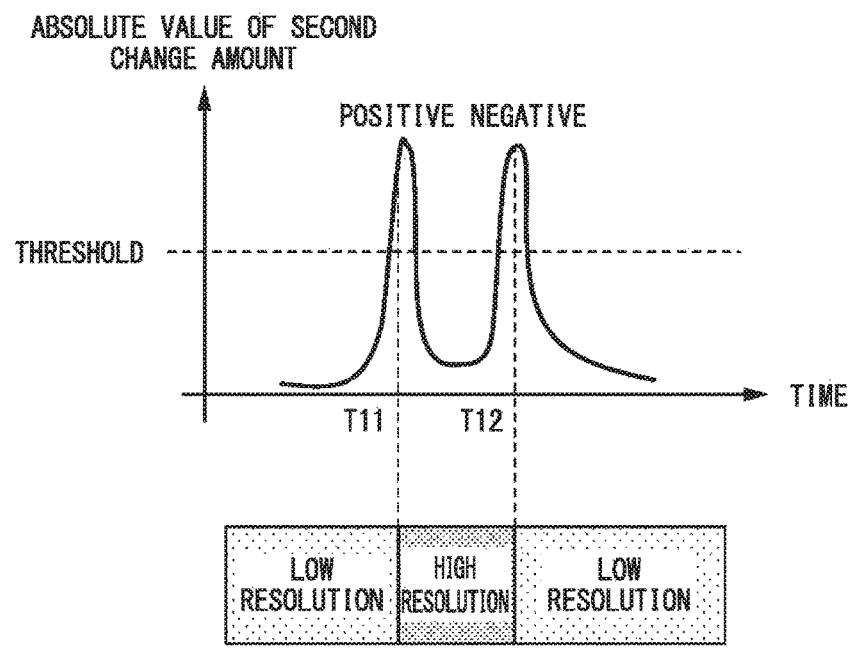
FIG. 2A is a graph showing a processing result of the imaging device according to the first embodiment of the present invention.
Figure 2B:
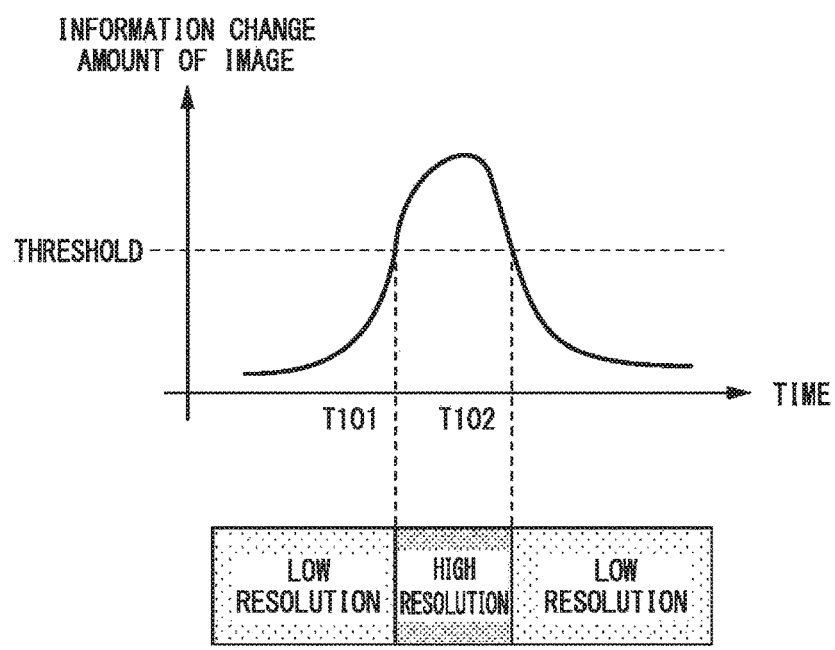
FIG. 2B is a graph showing a processing result of an imaging device of the related art.

A process of controlling the resolution of the imaging unit 100 will be described with reference to FIGS. 2A, 2B, 3A, and 3B. FIG. 2A shows a processing result of the imaging device 10. FIG. 2B shows a processing result of an imaging device of the related art. Horizontal axes of graphs in FIG. 2A and FIG. 2B indicate time. The vertical axis of the graph in FIG. 2A indicates an absolute value of the second change amount. The vertical axis of the graph in FIG. 2B indicates an information change amount of an image. FIGS. 2A and 2B show processing results when an information amount of only an important subject changes. For example, processing results when there are tree branches with a large number of leaves in a background of the important subject and the branches as well as the leaves do not move are the processing results shown in FIGS. 2A and 2B.

In the process of the imaging device 10 shown in FIG. 2A, the control unit 130 is in any one of two states including a low-resolution setting state and a high-resolution setting state, and repeatedly compares the absolute value of the second change amount with a threshold value. In a comparison up to a timing T11, the absolute value of the second change amount is determined to be smaller than the threshold value. As a result, the control unit 130 is in the low-resolution setting state and the resolution of the imaging unit 100 is set to a low resolution up to the timing T11. The low-resolution setting state is maintained until a condition that the absolute value of the second change amount be greater than or equal to the threshold value and a sign of the second change amount be positive is satisfied.

In a comparison at the timing T11, the absolute value of the second change amount is greater than or equal to the threshold value, and the sign of the second change amount is positive. In this case, the control unit 130 transitions from the low-resolution setting state to the high-resolution setting state, and sets the resolution of the imaging unit 100 to the high resolution. The high-resolution setting state is maintained until a condition that the absolute value of the second change amount be greater than or equal to the threshold value and the sign of the second change amount be negative is satisfied.

Subsequently, in a comparison at the timing T12, the absolute value of the second change amount is greater than or equal to the threshold value, and the sign of the second change amount is negative. In this case, the control unit 130 transitions from the high-resolution setting state to the low-resolution setting state, and sets the resolution of the imaging unit 100 to the low resolution. After the timing T12, the low-resolution setting state is maintained until a condition that the absolute value of the second change amount be greater than or equal to the threshold value and the sign of the second change amount be positive is satisfied.

In the process of the imaging device of the related art shown in FIG. 2B, a resolution of the imaging unit is set on the basis of a result of comparing the information change amount of the image with a threshold value. In a comparison up to a timing T101, the information change amount of the image is determined to be smaller than the threshold value. As a result, the resolution of the imaging unit is set to a low resolution up to the timing T101.

In the comparison at the timing T101, the information change amount of the image is determined to be greater than or equal to the threshold value. Therefore, the resolution of the imaging unit is set to a high resolution. After timing T101, the resolution of the imaging unit is not changed while the information change amount of the image is greater than or equal to the threshold value.

Subsequently, in a comparison at a timing T102, the information change amount of the image is determined to be smaller than the threshold value. Therefore, the resolution of the imaging unit is set to a low resolution. After the timing T102, the resolution of the imaging unit is not changed while the information change amount of the image is smaller than the threshold value.

In the process shown in FIGS. 2A and 2B, since only the important subject is included in the image, the resolution changes substantially similarly.

Figure 3A:
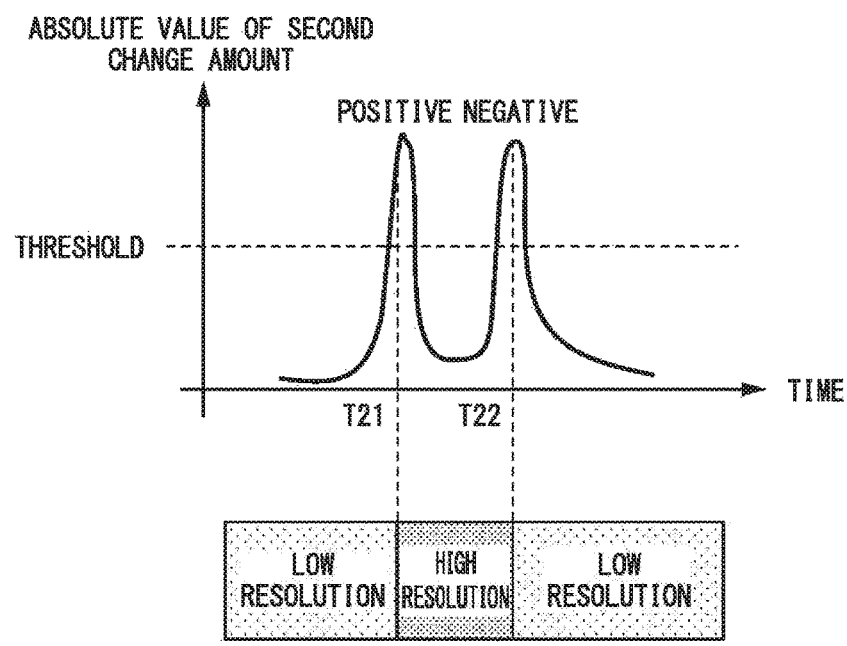
FIG. 3A is a graph showing a processing result of the imaging device according to the first embodiment of the present invention.
Figure 3B:
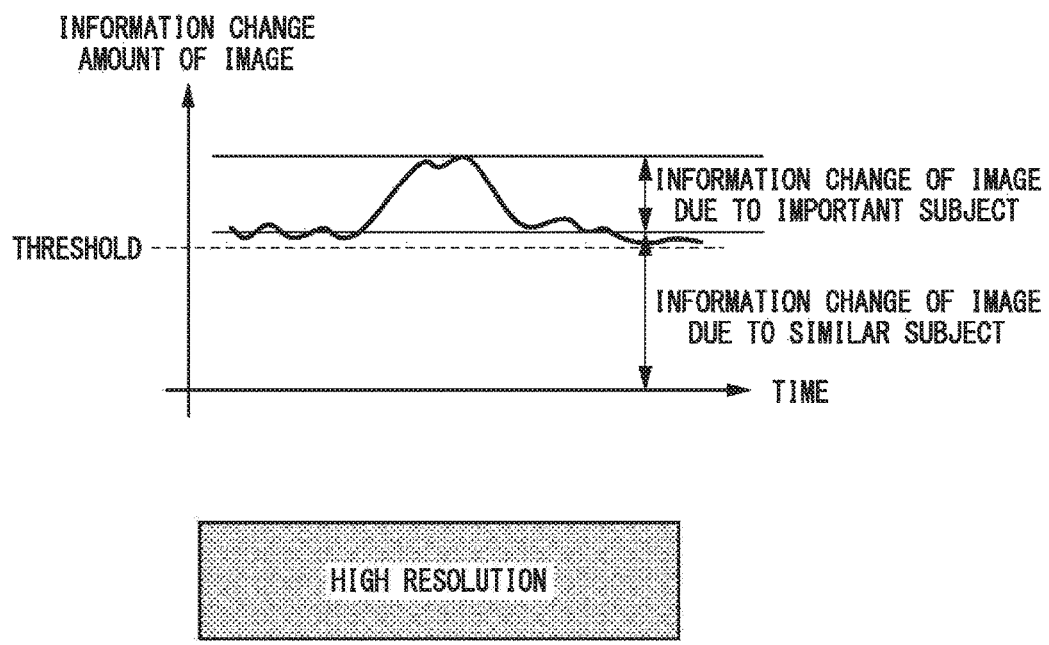
FIG. 3B is a graph showing a processing result of an imaging device of the related art.

FIG. 3A shows a processing result of the imaging device 10. FIG. 3B shows a processing result of an imaging device of the related art. Horizontal axes of graphs in FIGS. 3A and 3B indicate time. The vertical axis of the graph in FIG. 3A indicates an absolute value of a second change amount. The vertical axis of the graph in FIG. 3B indicates an information change amount of the image. FIGS. 3A and 3B show processing results when information amounts of an important subject and other subjects change. For example, processing results when there are tree branches with a large number of leaves in a background of the important subject, the branches are shaken, and the leaves are moved by wind are the processing results shown in FIGS. 3A and 3B.

In the process of the imaging device 10 shown in FIG. 3A, the resolution of the imaging unit 100 is changed, as in the process shown in FIG. 2A. That is, since the second change amount is smaller than the threshold value, the resolution of the imaging unit 100 is set to a low resolution up to a timing T21. At the timing T21, since it is determined that the absolute value of the second change amount is greater than or equal to the threshold value and the sign of the second change amount is positive, the resolution of the imaging unit 100 is set to a high resolution. The resolution of the imaging unit 100 is not changed from the timing T21 to a timing T22. At the timing T22, since it is determined that the absolute value of the second change amount is greater than or equal to the threshold value and the sign of the second change amount is negative, the resolution of the imaging unit 100 is set to a low resolution. After the timing T22, the resolution of the imaging unit 100 is not changed.

In the process of the imaging device of the related art shown in FIG. 3B, a resolution of the imaging unit is set on the basis of a result of comparing an information change amount of an image with a threshold value. As shown in FIG. 3B, the information change amount of the image is always greater than or equal to the threshold value. As a result, the resolution of the imaging unit is always set to a high resolution. A threshold value greater than the information change amount due to subjects other than the important subject may be set, but in this case, an information change amount of the important subject is likely to be overlooked.

In FIG. 3B, since the information change amount due to subjects other than the important subject is always greater than or equal to the threshold value, the resolution of the imaging unit is set to a high resolution regardless of the information change amount of the image due to the important subject. That is, in the process of the imaging device of the related art shown in FIG. 3B, the resolution of the imaging unit is incorrectly set due to an influence of subjects other than the important subject. On the other hand, in the process of the imaging device 10 shown in FIG. 3A, since the influence of subjects other than the important subject is eliminated from the second change amount, it is possible to appropriately set the resolution of the imaging unit 100.

According to this embodiment, the imaging device 10 includes an imaging unit 100 that continuously performs imaging to generate images of a plurality of frames of which the resolution is any one of a plurality of resolutions, a first change amount calculation unit 110 that calculates a first change amount that is an information change amount of the images of a plurality of frames, a second change amount calculation unit 120 that calculates a second change amount that is a temporal change amount of the first change amount, and a control unit 130 that controls the resolution of the imaging unit 100 on the basis of a result of comparing the second change amount with the threshold value.

In this embodiment, it is possible to reduce an influence of subjects other than the important subject on the control of the resolution by calculating the first change amount that is an information change amount of the image, calculating the second change amount that is a temporal change amount of the first change amount, and controlling the resolution of the imaging unit 100 on the basis of a result of comparing the second change amount with the threshold value. Further, it is possible to easily determine whether to increase or decrease the resolution of the imaging unit 100 by controlling the resolution of the imaging unit 100 on the basis of the sign of the second change amount.

Further, when the second change amount is smaller than the threshold value, it is possible to reduce power consumption of the imaging device 10 by setting the resolution of the imaging unit 100 to a resolution lower than that when the first change amount is greater than or equal to the threshold value. Further, it is possible to limit a data amount of an image to be recorded. Further, it is possible to limit a processing load of the imaging device 10.

Next, a modification example of this embodiment will be described.

(First Modification Example)

Figure 4:
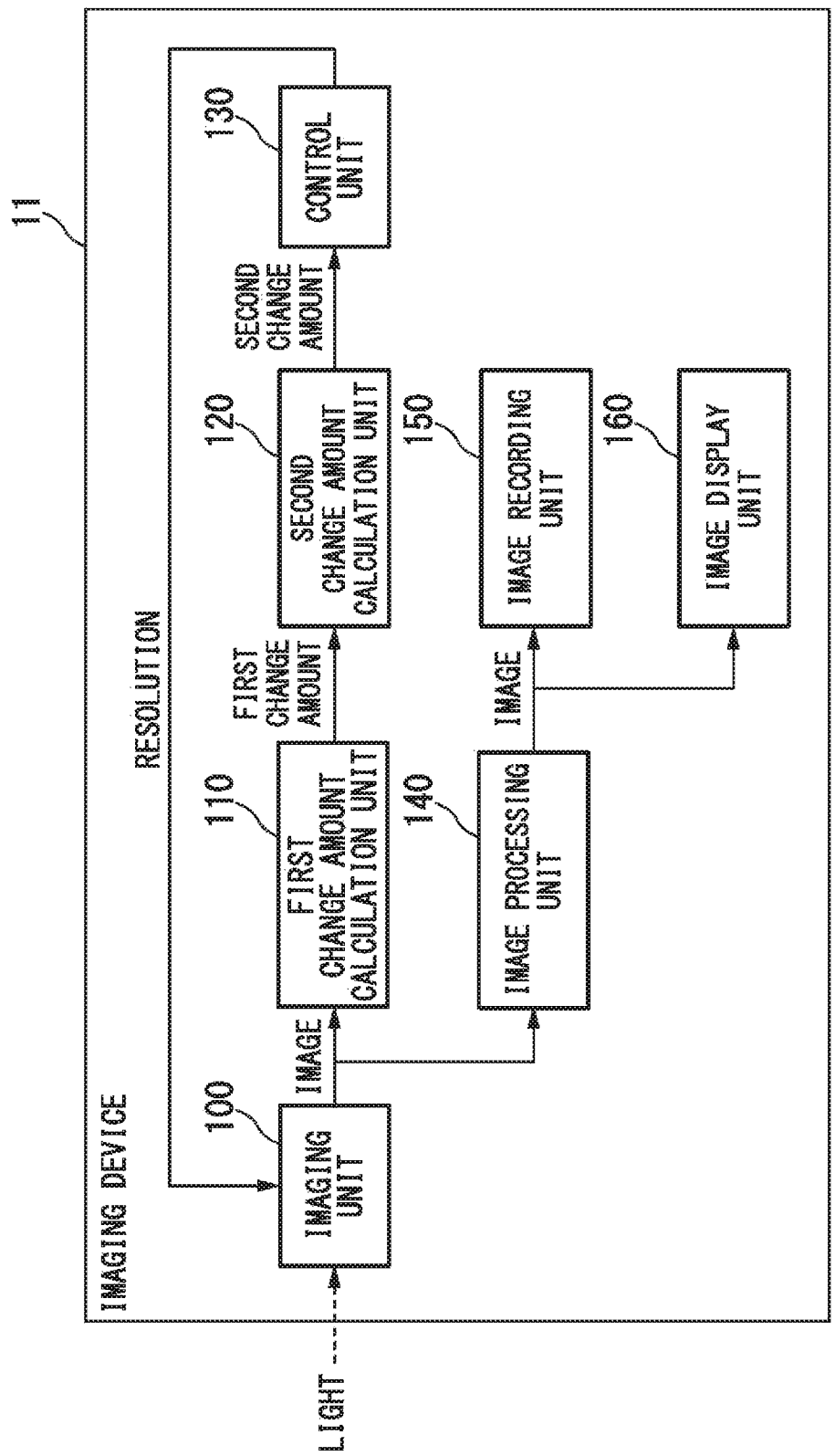
FIG. 4 is a block diagram showing a configuration of an imaging device according to a modification example of the first embodiment of the present invention.

FIG. 4 shows a configuration of an imaging device 11 that is a modification example of the imaging device 10. As shown in FIG. 4, the imaging device 11 includes an imaging unit 100, a first change amount calculation unit 110, a second change amount calculation unit 120, a control unit 130, an image processing unit 140, an image recording unit 150, and an image display unit 160. The imaging device 11 is configured similarly to a general camera such as a digital camera.

Hereinafter, only a configuration different from the configuration of the imaging device 10 will be described. The image processing unit 140 performs image processing on an image output from the imaging unit 100. The image recording unit 150 records the image processed by the image processing unit 140. The image display unit 160 displays the image processed by the image processing unit 140.

In this modification example, it is possible to reduce an influence of subjects other than an important subject on the control of the resolution of the imaging unit 100.

(Second Modification Example)

Figure 5:
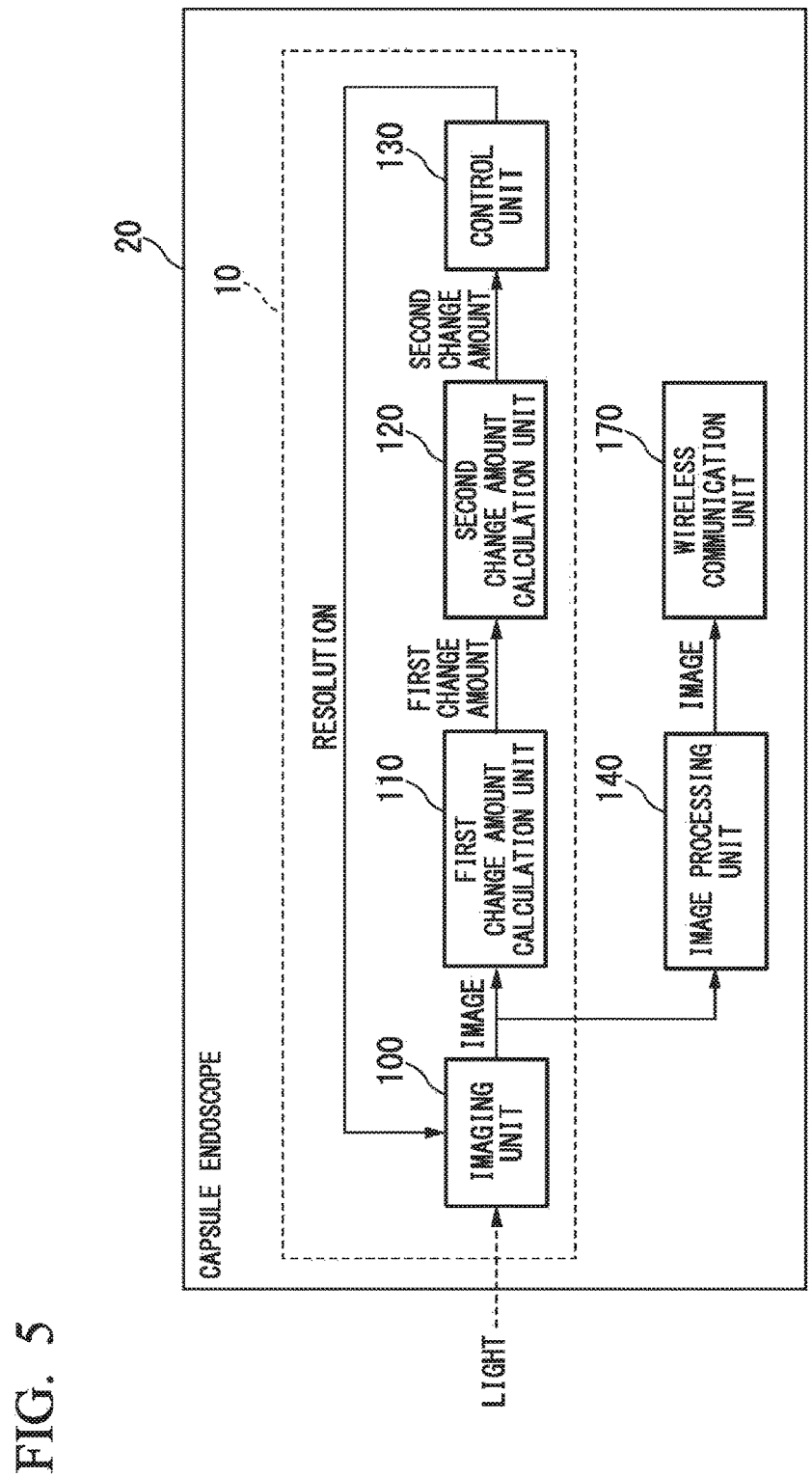
FIG. 5 is a block diagram showing a configuration of a capsule endoscope to which the imaging device according to the first embodiment of the present invention is applied.

FIG. 5 shows a configuration of a capsule endoscope 20 to which the imaging device 10 is applied. As shown in FIG. 5, the capsule endoscope 20 includes an imaging unit 100, a first change amount calculation unit 110, a second change amount calculation unit 120, a control unit 130, an image processing unit 140, and a wireless communication unit 170. That is, in this modification example, the capsule endoscope 20 includes an imaging device 10, an image processing unit 140, and a wireless communication unit 170.

Hereinafter, only a configuration different from the configurations of the imaging devices 10 and 11 will be described. The wireless communication unit 170 wirelessly transmits an image processed by the image processing unit 140 to the reception device.

For example, this embodiment is more effective when the capsule endoscope 20 is operated and is close to a lesion part or separated from the lesion part. In the inside of a living body, there are a change in an information amount of an image due to appearance and disappearance of an important subject (lesion part), and a change in an information amount of an image due to an imaging environment (background). The information amount of the image due to the imaging environment (background) continues to change not a little. In this modification example, it is possible to reduce an influence of subjects other than an important subject on the control of the resolution of the imaging unit 100.

(Third Modification Example)

This modification example will be described using the imaging device 11 shown in FIG. 4. In this modification example, the control unit 130 is in any one of three states including a low-resolution setting state, a medium-resolution setting state, and a high-resolution setting state. The control unit 130 controls the resolution of the imaging unit 100 on the basis of a result of comparing the information amount of the image with a first threshold value and a result of comparing the second change amount with a second threshold value. The control unit 130 can set any one of three states including the high-resolution setting state, the medium-resolution setting state, and the low-resolution setting state in the imaging unit 100.

Figure 6:
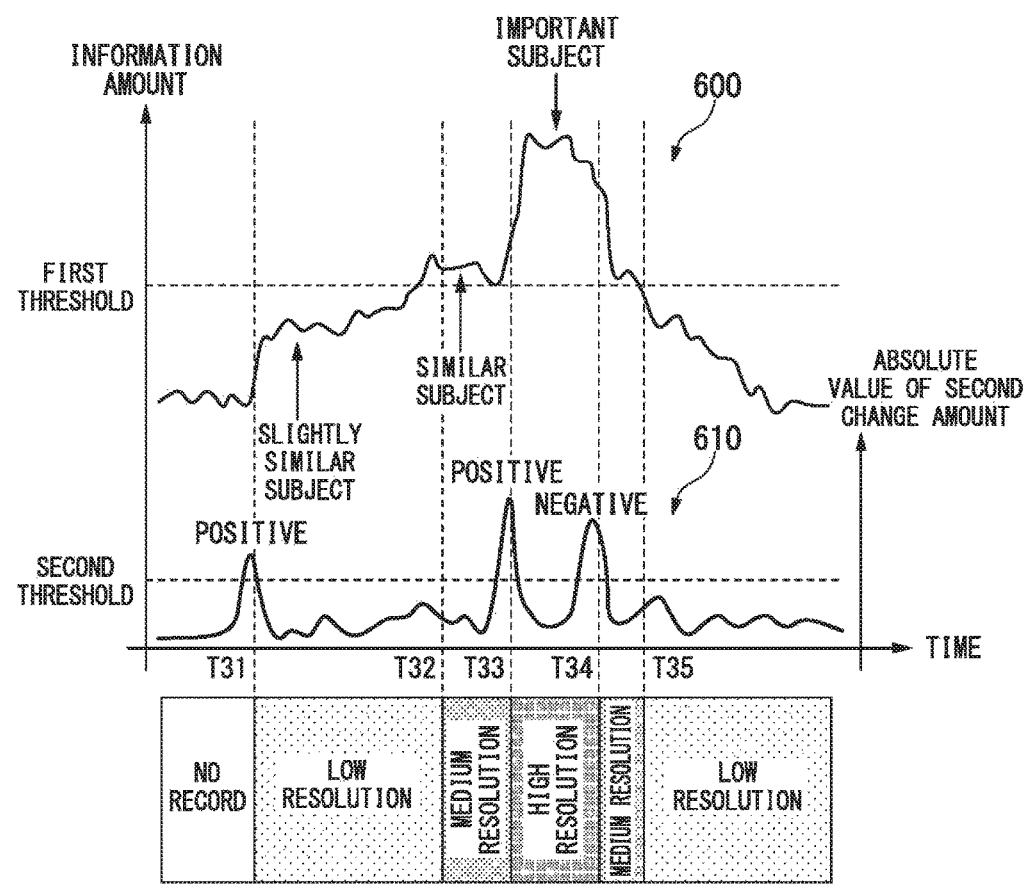
FIG. 6 is a graph showing a processing result of the imaging device according to the modification example of the first embodiment of the present invention.

FIG. 6 shows a processing result of the imaging device 11. In FIG. 6, a graph 600 showing the information amount of the image and a graph 610 showing the absolute value of the second change amount are shown. Horizontal axes of the two graphs in FIG. 6 indicate time. The vertical axis of the graph 600 in FIG. 6 indicates the absolute value of the information amount. The vertical axis of the graph 610 in FIG. 6 indicates the absolute value of the second change amount. FIG. 6 shows a processing result when an important subject and a plurality of subjects that are similar to the important subject and have different degrees of similarity are imaged.

FIG. 7 shows content of control performed by the control unit 130. In FIG. 7, content of control according to a result of comparing the information amount with the first threshold value and a result of comparing the absolute value of the second change amount with the second threshold value is defined. The first and second threshold values are not necessarily the same.

As shown in FIG. 7, the control unit 130 performs any one of eight types of processes (1) to (8) according to the comparison result. Hereinafter, each process will be described.

(1) When the information amount of the image is smaller than the first threshold value, the absolute value of the second change amount is smaller than the second threshold value, and a previously detected information amount of the image is smaller than the first threshold value, a subject included in the image is not an important subject, and there is no change in a scene. Therefore, the control unit 130 does not cause the image recording unit 150 to record the image.

(2) When the information amount of the image is smaller than the first threshold value, the absolute value of the second change amount is smaller than the second threshold value, and a previously detected information amount of the image is greater than or equal to the first threshold value, a possibility of the subject included in the image being the important subject becomes low. Therefore, the control unit 130 sets the resolution of the imaging unit 100 to a low resolution, and causes the image recording unit 150 to record the image.

(3) When the information amount of the image is smaller than the first threshold value, the absolute value of the second change amount is greater than or equal to the second threshold value, and a previously detected information amount of the image is smaller than the first threshold value, a process is different according to the sign of the second change amount. When the sign of the second change amount is negative, the possibility of the subject included in the image being the important subject becomes very low. Therefore, the control unit 130 does not cause the image recording unit 150 to record the image. When the sign of the second change amount is positive, the possibility of the subject included in the image being the important subject becomes very high. Therefore, the control unit 130 sets the resolution of the imaging unit 100 to a low resolution, and causes the image recording unit 150 to record the image.

(4) When the information amount of the image is smaller than the first threshold value, the absolute value of the second change amount is greater than or equal to the second threshold value, and a previously detected information amount of the image is greater than or equal to the first threshold value, the possibility of the subject included in the image being the important subject is low, but there is a change in a scene. Therefore, the control unit 130 sets the resolution of the imaging unit 100 to a low resolution and causes the image recording unit 150 to record the image.

(5) When the information amount of the image is greater than or equal to the first threshold value, the absolute value of the second change amount is smaller than the second threshold value, and a previously detected information amount of the image is smaller than the first threshold value, the control unit 130 causes the image recording unit 150 to record the image while maintaining the resolution that is set in the imaging unit 100.

(6) When the information amount of the image is greater than or equal to the first threshold value, the absolute value of the second change amount is smaller than the second threshold value, and a previously detected information amount of the image is greater than or equal to the first threshold value, there is a possibility of the subject included in the image being the important subject is low, but noise is likely to be included in the image. Therefore, the control unit 130 sets the resolution of the imaging unit 100 to a medium resolution and causes the image recording unit 150 to record the image.

(7) When the information amount of the image is greater than or equal to the first threshold value, the absolute value of the second change amount is greater than or equal to the second threshold value, and a previously detected information amount of the image is smaller than the first threshold value, the possibility of the subject included in the image being the important subject becomes very high. Therefore, the control unit 130 sets the resolution of the imaging unit 100 to a high resolution, and causes the image recording unit 150 to record the image.

(8) When the information amount of the image is greater than or equal to the first threshold value, the absolute value of the second change amount is greater than or equal to the second threshold value, and a previously detected information amount of the image is greater than or equal to the first threshold value, a process is different according to the sign of the second change amount. When the sign of the second change amount is positive, the possibility of the subject included in the image being the important subject becomes very high. Therefore, the control unit 130 sets the resolution of the imaging unit 100 to a resolution higher than the current resolution, and causes the image recording unit 150 to record the image. When the sign of the second change amount is negative, the possibility of the subject included in the image being the important subject becomes very low. Therefore, the control unit 130 sets the resolution of the imaging unit 100 to a resolution lower than the current resolution, and causes the image recording unit 150 to record the image.

When the absolute value of the second change amount is changed from a state in which the absolute value is greater than or equal to the second threshold value to a state in which the absolute value is smaller than the second threshold value, the resolution of the imaging unit 100 is not changed regardless of a comparison result.

An operation of the imaging device 11 when an information amount of the image changes as shown in the graph 600 shown in FIG. 6 and the absolute value of the second change amount changes as shown in the graph 610 shown in FIG. 6 will be described. After the imaging device 11 starts the process, the control unit 130 sets the resolution of the imaging unit 100 to an arbitrary resolution. For example, the control unit 130 sets the resolution of the imaging unit 100 to a low resolution. In this case, the information amount of the image is smaller than a first threshold value, and the absolute value of the second change amount is smaller than the second threshold value. Therefore, the control unit 130 does not cause the image recording unit 150 to record the image, as shown in the process (1) of FIG. 7. Thereafter, since the comparison result does not change, the state in which no image is recorded continues.

In a comparison at a timing T31, it is determined that the information amount of the image is smaller than the first threshold value, the absolute value of the second change amount is greater than or equal to the second threshold value, and the previously detected information amount of the image is smaller than the first threshold value. Further, it is determined that the sign of the second change amount is positive. In this case, the control unit 130 sets the resolution of the imaging unit 100 to a low resolution, and causes the image recording unit 150 to record the image, as shown in the process (3) in FIG. 7. Thereafter, the absolute value of the second change amount becomes smaller than the second threshold value, but the resolution of the imaging unit 100 is not changed.

Subsequently, in a comparison at a timing T32 next to a timing at which it is detected that the information amount of the image is greater than or equal to the first threshold value, it is determined that the information amount of the image is greater than or equal to the first threshold value, an absolute value of the second change amount is smaller than the second threshold value, and the previously detected information amount of the image is greater than or equal to the first threshold value. In this case, the control unit 130 sets the resolution of the imaging unit 100 to a medium resolution, and causes the image recording unit 150 to record the image, as shown in the process (6) in FIG. 7. Thereafter, since the comparison result does not change, the resolution of the imaging unit 100 is maintained at the medium resolution.

Subsequently, in a comparison at a timing T33, it is determined that the information amount of the image is greater than or equal to the first threshold value, an absolute value of the second change amount is greater than or equal to the second threshold value, and the previously detected information amount of the image is greater than or equal to the first threshold value. Further, it is determined that the sign of the second change amount is positive. In this case, the control unit 130 increases the resolution of the imaging unit 100 and causes the image recording unit 150 to record the image, as shown in the process (8) in FIG. 7. That is, the control unit 130 sets the resolution of the imaging unit 100 to a high resolution. Thereafter, the absolute value of the second change amount becomes smaller than the second threshold value, but the resolution of the imaging unit 100 is not changed.

Subsequently, in a comparison at a timing T34, it is determined that the information amount of the image is greater than or equal to the first threshold value, the absolute value of the second change amount is greater than or equal to the second threshold value, and the previously detected information amount of the image is greater than or equal to the first threshold value. Further, the sign of the second change amount is determined to be negative. In this case, the control unit 130 decreases the resolution of the imaging unit 100 and causes the image recording unit 150 to record the image, as shown in the process (8) of FIG. 7. That is, the control unit 130 sets the resolution of the imaging unit 100 to a medium resolution. Thereafter, the absolute value of the second change amount becomes smaller than the second threshold value, but the resolution of the imaging unit 100 is not changed.

Subsequently, in a comparison at a timing T35, it is determined that the information amount of the image is smaller than the first threshold value, the absolute value of the second change amount is smaller than the second threshold value, and the previously detected information amount of the image is greater than or equal to the first threshold value. In this case, the control unit 130 sets the resolution of the imaging unit 100 to a low resolution, as shown in the process (2) in FIG. 7. Thereafter, since the comparison result does not change, the resolution of the imaging unit 100 is maintained at the low resolution.

In this modification example, it is possible to reduce an influence of subjects other than an important subject on the control of the resolution of the imaging unit 100. Further, it is possible to more finely control the resolution of the imaging unit 100 by controlling the resolution of the imaging unit 100 on the basis of the result of comparing the information amount of the image with the first threshold value and the result of comparing the second change amount with the second threshold value. Further, it is possible to easily determine whether to increase or decrease the resolution of the imaging unit 100 by controlling the resolution of the imaging unit 100 on the basis of the sign of the second change amount.

The control unit 130 may provide a plurality of first threshold values and a plurality of second threshold values. The control unit 130 may control the resolution of the imaging unit 100 on the basis of a result of comparing the information amount of the image with the plurality of threshold values, and a result of comparing the second change amount with the plurality of threshold values. Accordingly, it possible to more finely control the resolution of the imaging unit 100.

(Second Embodiment)

Next, a second embodiment of the present invention will be described. This embodiment will be described using the imaging device 10 shown in FIG. 1. In this embodiment, the imaging unit 100 generates a plurality of types of images having different resolutions on the basis of pixel signals in which exposure timings are the same.

Figure 8:
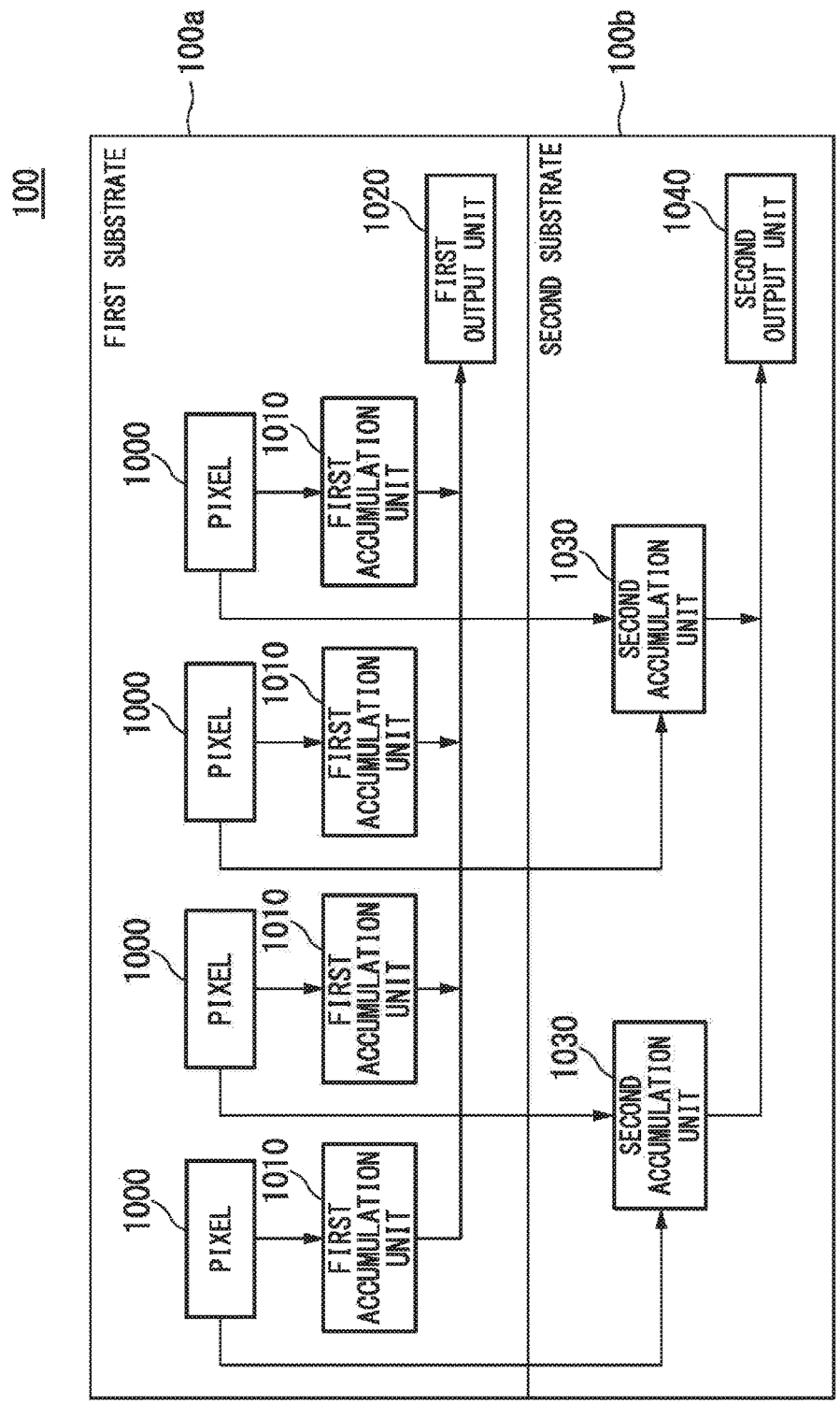
FIG. 8 is a block diagram showing a configuration of an imaging unit included in an imaging device according to a second embodiment of the present invention.

FIG. 8 shows a configuration of the imaging unit 100. As shown in FIG. 8, the imaging unit 100 includes a first substrate 100*a* and a second substrate 100*b*. For example, the first substrate 100*a* and the second substrate 100*b* overlap in a state in which main surfaces thereof face each other. Further, the first substrate 100*a* and the second substrate 100*b* are electrically connected to each other.

The first substrate 100*a* includes a plurality of pixels 1000, a plurality of first accumulation units 1010, and a first output unit 1020. The plurality of pixels 1000 include a photoelectric conversion element, and generate first pixel signals based on incident light. The plurality of first accumulation units 1010 accumulate the first pixel signals output from the plurality of pixels 1000. The first output unit 1020 outputs images of a plurality of frames composed of the first pixel signals accumulated in the plurality of first accumulation units 1010. The respective images of the plurality of frames output from the first output unit 1020 are composed of the first pixel signals accumulated in the plurality of first accumulation units 1010.

The second substrate 100*b* includes a plurality of second accumulation units 1030 and a second output unit 1040. The plurality of second accumulation units 1030 accumulate the second pixel signals obtained by adding the first pixel signals output from the plurality of pixels 1000 for every plurality of first pixel signals. For example, as shown in FIG. 8, two first pixel signals are added and stored in the second accumulation unit 1030. The second output unit 1040 outputs the images of the plurality of frames composed of the second pixel signals accumulated in the plurality of second accumulation units 1030. Each of the images of the plurality of frames output from the second output unit 1040 is composed of the second pixel signals accumulated in the plurality of second accumulation units 1030.

The number of first pixel signals constituting the image output from the first output unit 1020 is different from the number of second pixel signals constituting the image output from the second output unit 1040. That is, a resolution of the image output from the first output unit 1020 is different from a resolution of the image output from the second output unit 1040. In the example shown in FIG. 8, the resolution of the image output from the second output unit 1040 is half of the resolution of the image output from the first output unit 1020. The number of first pixel signals to be added may be, for example, 4.

The plurality of first accumulation units 1010, the first output unit 1020, the plurality of second accumulation units 1030, and the second output unit 1040 may be arranged in either the first substrate 100a or the second substrate 100b regardless of an arrangement of other configurations. For example, both of the first output unit 1020 and the second output unit 1040 may be arranged in the first substrate 100a or the second substrate 100b.

Further, the imaging unit 100 may include three or more substrates. For example, the imaging unit 100 may further include a plurality of third accumulation units that accumulate third pixel signals obtained by adding first pixel signals output from the plurality of pixels 1000 for every plurality of first pixel signals, and a third output unit that outputs images of a plurality of frames composed of the third pixel signals accumulated in the plurality of third accumulation units. A resolution of the image output from the third output unit is different from the resolution of the image output from the first output unit 1020 and the resolution of the image output from the second output unit 1040.

Figure 9:
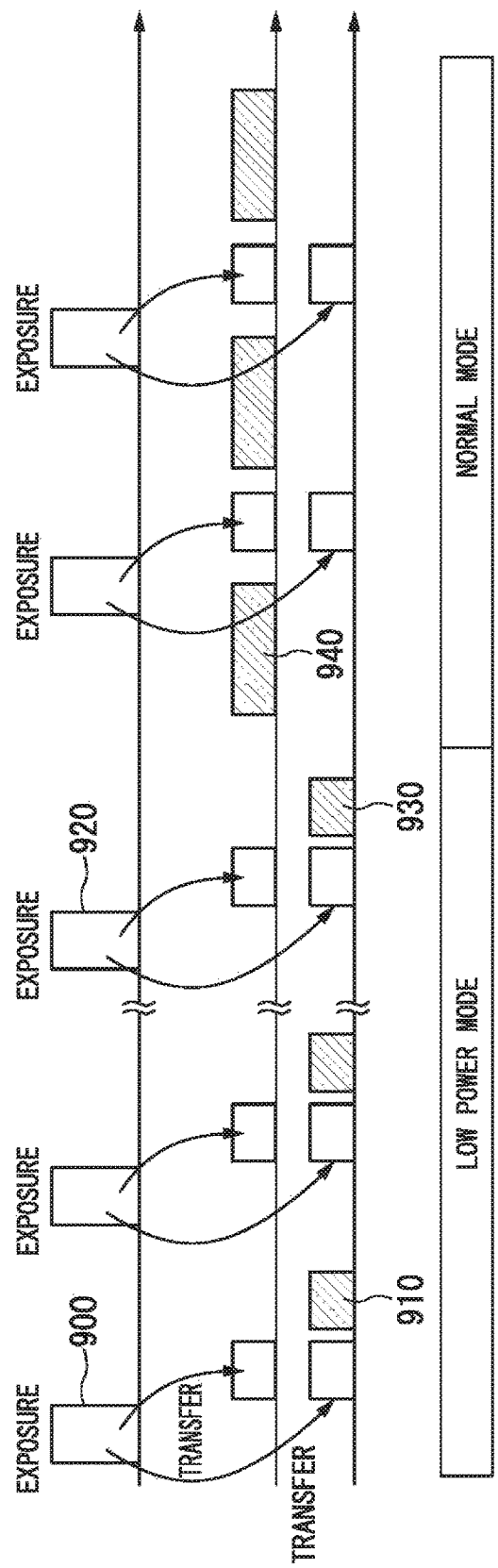
FIG. 9 is a timing chart showing a processing timing of signals in the imaging unit included in the imaging device according to the second embodiment of the present invention.

Next, an operation of the imaging unit 100 will be described with reference to FIG. 9. FIG. 9 shows a signal processing timing in the imaging unit 100. A right direction in FIG. 9 is a progress direction of time.

The imaging unit 100 operates in any one of a normal mode and a low power mode in which power consumption is lower than that in the normal mode. In the low power mode, a resolution lower than the resolution that is set in the imaging unit 100 in the normal mode is set in the imaging unit 100. In FIG. 9, the imaging unit 100 starts an operation in the low power mode.

By exposure of a plurality of pixels 1000, first pixel signals are generated in the respective pixels 1000. The first pixel signals generated by exposure 900 are simultaneously transferred to the first accumulation unit 1010 and the second accumulation unit 1030, and the transferred first pixel signals are accumulated in the respective accumulation units. When a plurality of first pixel signals are transferred to the second accumulation unit 1030, the first pixel signals are added. A second pixel signal obtained by adding the plurality of first pixel signals is accumulated in the second accumulation unit 1030.

In the low power mode, the second output unit 1040 outputs an image 910 based on the second pixel signal accumulated in the second accumulation unit 1030. The second output unit 1040 repeatedly outputs an image while the mode of the imaging unit 100 is the low power mode.

After an image 930 based on the second image signal accumulated in the second accumulation unit 1030 is output, the mode of the imaging unit 100 is changed from the low power mode to the normal mode. The first output unit 1020 outputs an image 940 based on the first pixel signals accumulated in the first accumulation unit 1010 immediately after the mode of the imaging unit 100 becomes the normal mode. The first output unit 1020 repeatedly outputs an image while the mode of the imaging unit 100 is the normal mode.

The image 930 to be output at the end of an operation in the low power mode is an image based on the second pixel signal obtained by adding the first pixel signals generated by exposure 920. Further, the image 940 to be first output in the normal mode is an image based on the first pixel signals generated by the exposure 920.

In this embodiment, the first pixel signals are simultaneously transferred from the plurality of pixels 1000 to the first accumulation unit 1010 and the second accumulation unit 1030. Therefore, the first pixel signals accumulated in the first accumulation unit 1010 and the first pixel signals that are sources of the second pixel signals accumulated in the second accumulation unit 1030 are signals generated by the exposure at the same timing.

In this embodiment, it is possible to obtain a plurality of images having different resolutions corresponding to exposure at the same timing with respect to the control of the resolution of the imaging unit 100. Therefore, in the imaging device 10 that controls the resolution of the image on the basis of the temporal change amount of the information change amount of the image, when the resolution of the imaging unit 100 is changed, it is possible to obtain an image having a changed resolution without re-exposure at the changed resolution. Therefore, imaging of an important subject is hard to miss. Particularly, when the resolution of the imaging unit 100 is changed to a higher resolution, imaging of an important subject is hard to miss at a timing at which the resolution is changed, that is, a timing at which a movement of the important subject is greatly changed.

While preferred embodiments of the invention have been described and shown above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:
1. An imaging device, comprising:
an imaging unit that continuously performs imaging to generate images of a plurality of frames of which the resolution is any one of a plurality of resolutions by exposure at the same timing;
a first change amount calculation circuit that calculates a first change amount that is an information change amount of the images of a plurality of frames by calculating differences between images captured at different times;
a second change amount calculation circuit that calculates a second change amount that is a temporal change amount of the first change amount by calculating a change amount of first change amounts that are continuously calculated by the first change amount calculation circuit; and
a control circuit that controls a resolution of the imaging unit on the basis of a result of comparing the second change amount with a threshold value and a result of discriminating a sign of the second change amount,
wherein the imaging unit includes
a first substrate; and
a second substrate,
the first substrate includes
a plurality of pixels that generate first pixel signals based on incident light;
a plurality of first accumulation units that accumulate the first pixel signals output from the plurality of pixels; and a first output unit that outputs the images of the plurality of frames composed of the first pixel signals accumulated in the plurality of first accumulation units;

the second substrate includes a plurality of second accumulation units that accumulate second pixel signals obtained by adding the first pixel signals output from the plurality of pixels for every plurality of pixel signals; and a second output unit that outputs the images of the plurality of frames composed of the second pixel signals accumulated in the plurality of second accumulation units, the first substrate and the second substrate are electrically connected to each other, when the second change amount is smaller than a threshold value, the control circuit causes the second output unit to output the image composed of the second pixel signals, and when the second change amount is greater than or equal to the threshold value, the control circuit causes the first output unit to output the image composed of the first pixel signals.

2. A capsule endoscope comprising the imaging device according to claim 1.

* * * * *